United States Patent
Molaei et al.

(10) Patent No.: US 9,833,310 B2
(45) Date of Patent: *Dec. 5, 2017

(54) MEDICAL DEVICES INCLUDING METALLIC FILM AND AT LEAST ONE FILAMENT

(71) Applicant: Boston Scientific SciMed, Inc., Maple Grove, MN (US)

(72) Inventors: Masoud Molaei, Mountain View, CA (US); Beren W. Correa, Fremont, CA (US)

(73) Assignee: Boston Scientific Scimed, Inc., Maple Grove, MN (US)

( * ) Notice: Subject to any disclaimer, the term of this patent is extended or adjusted under 35 U.S.C. 154(b) by 257 days.

This patent is subject to a terminal disclaimer.

(21) Appl. No.: 14/519,685

(22) Filed: Oct. 21, 2014

(65) Prior Publication Data

US 2015/0039077 A1 Feb. 5, 2015

Related U.S. Application Data

(63) Continuation of application No. 13/031,923, filed on Feb. 22, 2011, now Pat. No. 8,864,815, which is a continuation of application No. 11/025,684, filed on Dec. 29, 2004, now Pat. No. 7,901,447.

(51) Int. Cl.
| | | |
|---|---|---|
| *A61F 2/06* | (2013.01) | |
| *A61F 2/07* | (2013.01) | |
| *A61F 2/90* | (2013.01) | |
| *A61L 31/02* | (2006.01) | |
| *A61L 31/14* | (2006.01) | |

(52) U.S. Cl.
CPC .............. *A61F 2/07* (2013.01); *A61F 2/90* (2013.01); *A61L 31/022* (2013.01); *A61L 31/143* (2013.01); *A61F 2002/072* (2013.01); *A61F 2002/075* (2013.01); *Y10S 623/901* (2013.01)

(58) Field of Classification Search
CPC .......... A61F 2002/072; A61F 2002/075; A61F 2/07; A61F 2002/9511
USPC ..... 623/1.15, 1.11, 1.12; 53/397, 399; 47/72
See application file for complete search history.

(56) References Cited

U.S. PATENT DOCUMENTS

| | | | | |
|---|---|---|---|---|
| 5,843,163 A | * | 12/1998 | Wall ......................... | A61F 2/92 600/3 |
| 6,802,858 B2 | * | 10/2004 | Gambale .................. | A61F 2/06 623/1.15 |
| 2003/0050684 A1 | * | 3/2003 | Abrams .................... | A61F 2/95 623/1.11 |
| 2004/0054396 A1 | * | 3/2004 | Hartley ..................... | A61F 2/07 623/1.13 |
| 2004/0093017 A1 | * | 5/2004 | Chanduszko ...... | A61B 17/0057 606/200 |
| 2006/0052865 A1 | * | 3/2006 | Banas ....................... | A61F 2/07 623/1.44 |

* cited by examiner

*Primary Examiner* — Corrine McDermott
*Assistant Examiner* — Majid Jamialahmadi

(57) ABSTRACT

Medical devices, such as endoprostheses, and methods of making the devices are disclosed. The medical device can include a composite cover formed of a deposited metallic film. The cover may include one or more filaments, e.g., wires, which cooperate with the film to provide desirable mechanical properties. The wires may be integrated with the film by depositing the film over the wires.

20 Claims, 10 Drawing Sheets

MEDICAL DEVICES INCLUDING METALLIC FILM AND AT LEAST ONE FILAMENT

CROSS REFERENCE TO RELATED APPLICATIONS

This application is a continuation of U.S. application Ser. No. 13/031,923, filed Feb. 22, 2011, which is a continuation of U.S. application Ser. No. 11/025,684, filed Dec. 29, 2004, now U.S. Pat. No. 7,901,447, which issued Mar. 8, 2011. The disclosure of the prior application is hereby incorporated by reference in its entirety.

FIELD OF THE INVENTION

The invention relates to medical devices, such as endoprostheses, and methods of making the devices.

BACKGROUND

The body includes various passageways such as arteries, other blood vessels, and other body lumens. These passageways sometimes become occluded or weakened. For example, the passageways can be occluded by a tumor, restricted by plaque, or weakened by an aneurysm. When this occurs, the passageway can be reopened or reinforced, or even replaced, with a medical endoprosthesis. An endoprosthesis is typically a tubular member that is placed in a lumen in the body. Endoprostheses can be delivered inside the body by a catheter that supports the endoprosthesis in a compacted or reduced-size form as the endoprosthesis is transported to a desired site. Upon reaching the site, the endoprosthesis is expanded, for example, so that it can contact the walls of the lumen.

The expansion mechanism may include forcing the endoprosthesis to expand radially. For example, the expansion mechanism can include the catheter carrying a balloon, which carries a balloon-expandable endoprosthesis. The balloon can be inflated to deform and to fix the expanded endoprosthesis at a predetermined position in contact with the lumen wall. The balloon can then be deflated, and the catheter withdrawn.

In another delivery technique, the endoprosthesis is formed of an elastic material that can be reversibly compacted and expanded, e.g., elastically or through a material phase transition. During introduction into the body, the endoprosthesis is restrained in a radially compacted condition. Upon reaching the desired implantation site, the restraint is removed, for example, by retracting a restraining device such as an outer sheath, enabling the endoprosthesis to self-expand by its own internal elastic restoring force.

SUMMARY OF THE INVENTION

The invention relates to medical devices, such as endoprostheses, and methods of making the devices. Exemplary endoprostheses include stents, covered stents, and stent-grafts.

In some embodiments, an endoprosthesis includes a deposited metallic film defining first and second opposed surfaces and a thickness of less than about 50 µm therebetween and at least one metal filament. The at least one filament defines a length. At least a portion of the filament along its length is embedded within the deposited metallic film between its first and second surfaces.

The deposited metallic film may include deposited titanium and nickel, e.g., an alloy including nickel and titanium.

The deposited film may have a substantially tubular shape defining a longitudinal axis. The at least one filament may extend, e.g., linearly or helically, generally along the longitudinal axis.

The tubular shape of the film may define a length along the longitudinal axis and the length of the filament may be at least about 30% of the length of the tubular shape of the film.

The endoprosthesis may include a plurality of filaments each defining a length. At least a portion of each wire along its length may be embedded within the metallic film between the first and second surfaces. Each filament may extend generally along the longitudinal axis. The length of each filament may be at least 30% of the length of the tubular shape of the film.

At least 75% of the filament along its length may be embedded within the metallic film between the first and second surfaces of the metallic film.

The filament, along its length, may include a plurality of embedded portions and at least one non-embedded portion. Each embedded portion may be embedded within the metallic film between the first and second surfaces of the metallic film. Adjacent embedded portions may be spaced apart by a non-embedded portion of the filament.

The substantially tubular shape may define a circumference. The at least one filament may extend at least partially about the circumference.

The at least one filament may be an alloy comprising nickel and titanium.

The metallic film and the at least one filament may each have a respective tensile strength, with the tensile strength of the filament being greater than the tensile strength of the metallic film. The metallic film and the at least one filament may each have a respective, different shape set configuration.

The endoprosthesis may include a stent body. The stent body and the deposited film may be generally concentric.

In some embodiments, an endoprosthesis includes a cover including at least one deposited metallic film. The cover defines first and second opposed metallic film edges. The first and second opposed metallic film edges each define a channel. At least one filament may extend along the channel of each opposed metallic film edge.

The deposited metallic film may include deposited nickel and titanium, e.g., an alloy including nickel and titanium.

The cover may have a substantially tubular shape defining a longitudinal axis. The at least one filament may extend generally parallel to the longitudinal axis. The tubular shape may define a length along the longitudinal axis. The length of the filament may be at least about 30% of the length of the tubular shape.

The first and second opposed edges may each define at least one offset tab. The channel of each opposed edge may be formed by the offset tab.

The first and second opposed edges may each define a plurality of channels. Each channel may be formed by a respective offset tab. The filament may extend through at least some of the channels of each opposed edge.

The endoprosthesis may include a stent body. At least a portion of the at least one filament and at least a portion of the stent body may be secured together.

The filament may define a longitudinal axis. An engagement between at least one of the channels and the filament may restrict movement of the filament along its longitudinal axis with respect to the at least one of the channels. The filament may have freedom of movement along its length with respect to at least one of the channels.

The first and second opposed edges may be a first pair of opposed edges and metallic film of the cover may define a plurality of pairs of first and second opposed edges. Each edge of each pair may define at least one channel. A respective filament may extend through the channel of each opposed edge of each pair. Each pair of opposed edges may extend generally along the longitudinal axis. Each filament may have a length at least about 30% of the length of the tubular shape. The first and second edges of each pair of opposed edges may have at least some relative freedom of movement with respect to a circumference of the cover.

In one aspect, the invention features an endoprosthesis including a metallic film, e.g., a vapor deposited film, including nickel, titanium, and chromium. A ratio of a weight of chromium of the metallic film to a combined weight of nickel, titanium, and chromium of the metallic film is at least 0.001 and can be less than 0.0075.

Other aspects, features, and advantages of the invention will be apparent from the description of the preferred embodiments thereof and from the claims.

BRIEF DESCRIPTION OF THE FIGURES

FIG. 3b is a cross-sectional view of the endoprosthesis of FIG. 3a.

FIG. 10b is a cross-sectional view of the endoprosthesis of FIG. 10a.

DETAILED DESCRIPTION

Figure 1:
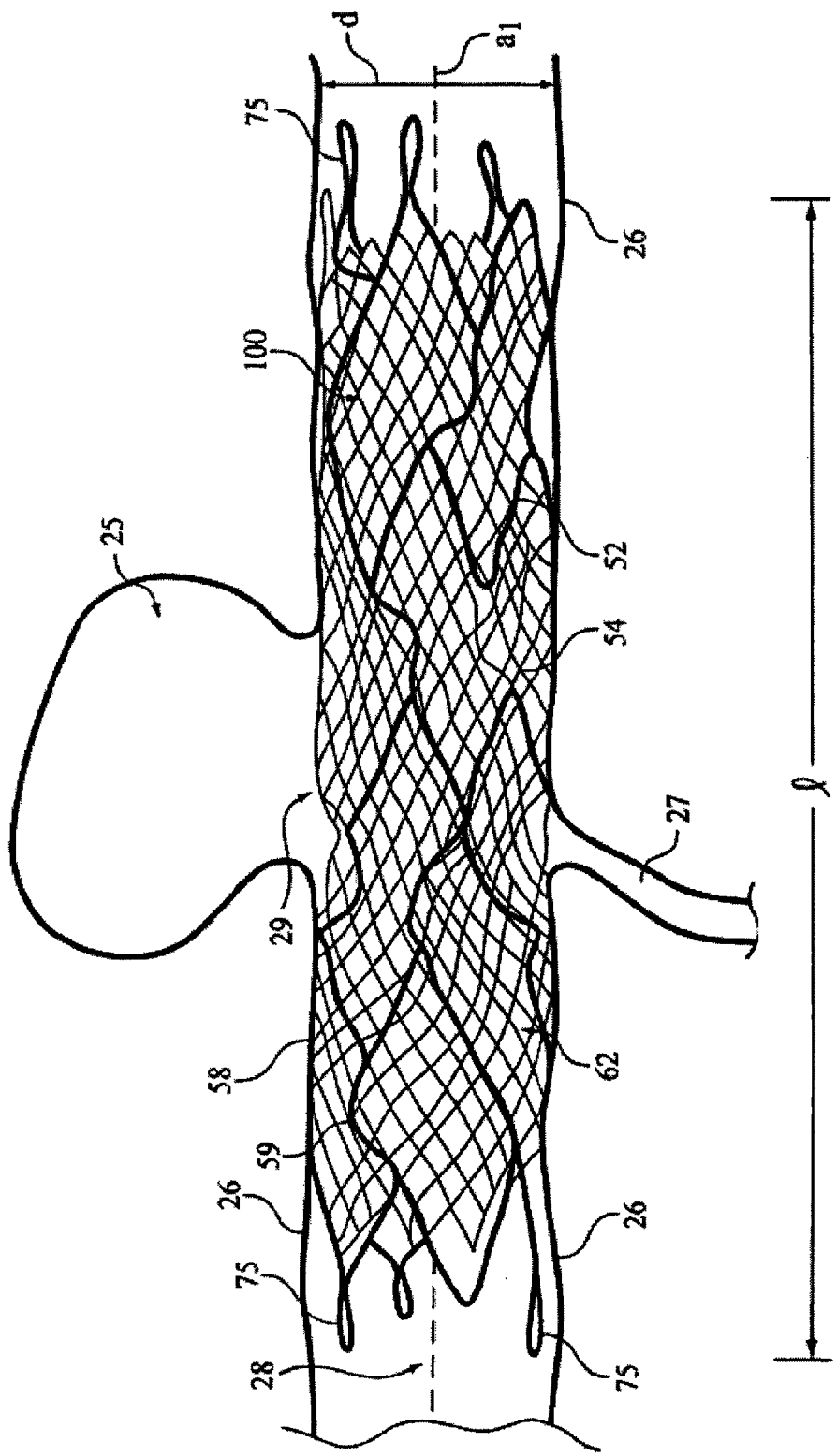
FIG. 1 is a side view of an endoprosthesis in a radially expanded state as deployed within a body passage adjacent an aneurysm.

Referring to FIG. 1, an endoprosthesis 100 is deployed within a body passage, e.g., within a vessel weakened by an aneurysm, e.g., an aneurysm 25 of a vessel 26 of a human brain. Endoprosthesis 100 includes a framework, e.g., a stent body 52, covered by a tubular member or cover 54. The stent body provides a relatively rigid framework that secures the endoprosthesis at the treatment site. The framework defines relatively large openings or fenestrations that contribute to the mechanical properties of the stent. The cover 54 is relatively thin and flexible and includes smaller fenestrations that contribute to the mechanical properties of the cover and occlude the fenestrations of the stent.

The endoprosthesis 100 modifies an amount or velocity of blood passing between vessel 26 and aneurysm 25. For example, prosthesis 100 can be deployed to reduce or block blood flow between vessel 26 and aneurysm 25. The endoprosthesis can also reduce blood flow from a feeder vessel 27. If so deployed, prosthesis 100 may sufficiently reduce blood flow to allow clotting or other healing processes to take place within aneurysm 25 and/or opening 29. Tubular member 54 can provide a greater attenuation of the blood flow into the aneurysm 25 than stent body 52 alone. Endoprosthesis 100, however, can allow some flow to pass between vessel 26 and aneurysm 25 even while providing some reduction in the rate and/or volume of flow. Prosthesis 100 can also (or alternatively) allow blood to pass between vessel 26 containing the prosthesis and adjacent vessels, e.g., feeder vessel 27, while still providing reduced flow with respect to the aneurysm.

Figure 2A:
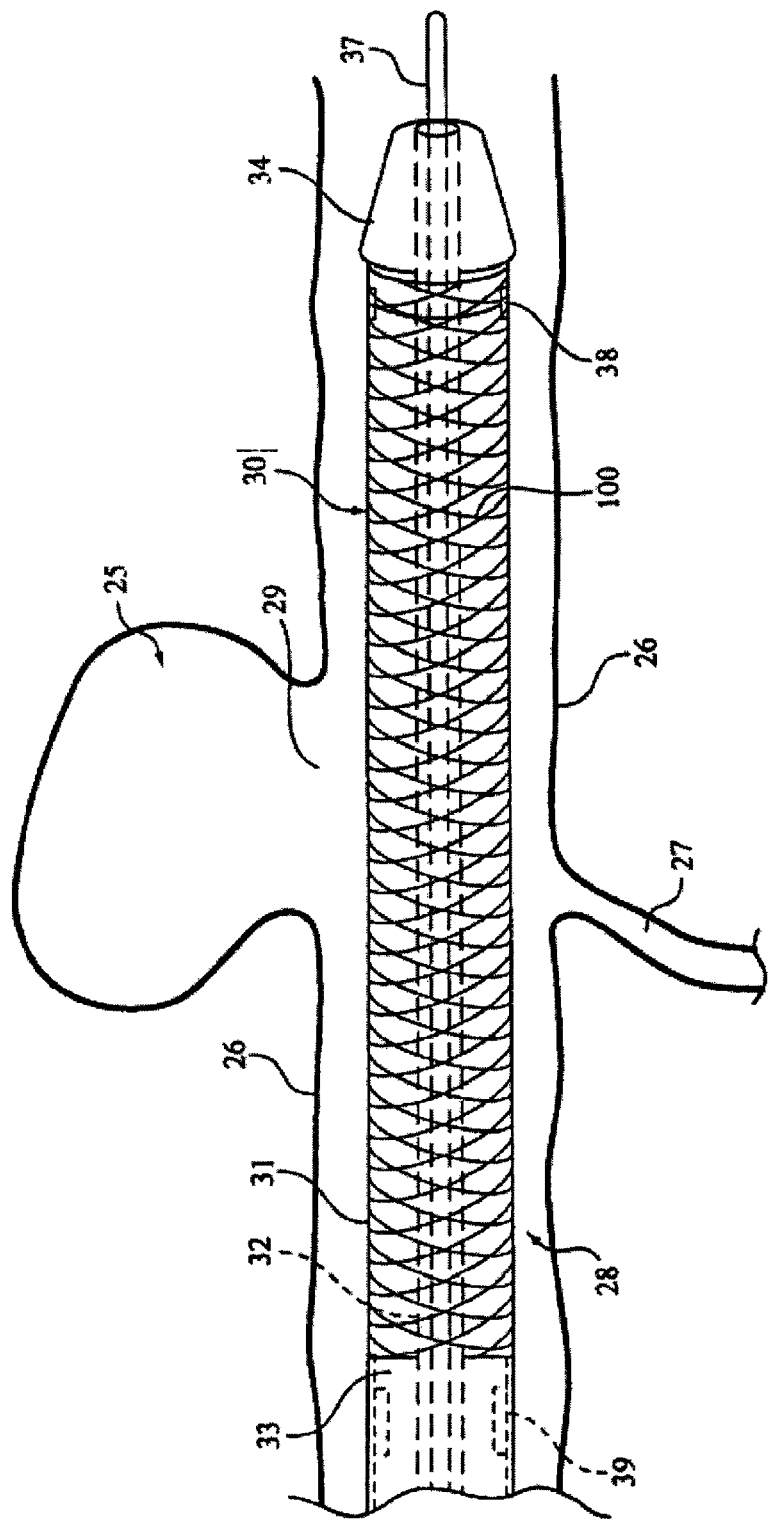
FIG. 2a is a side view of a distal portion of a deployment device prior to radial expansion of the endoprosthesis.
Figure 2B:
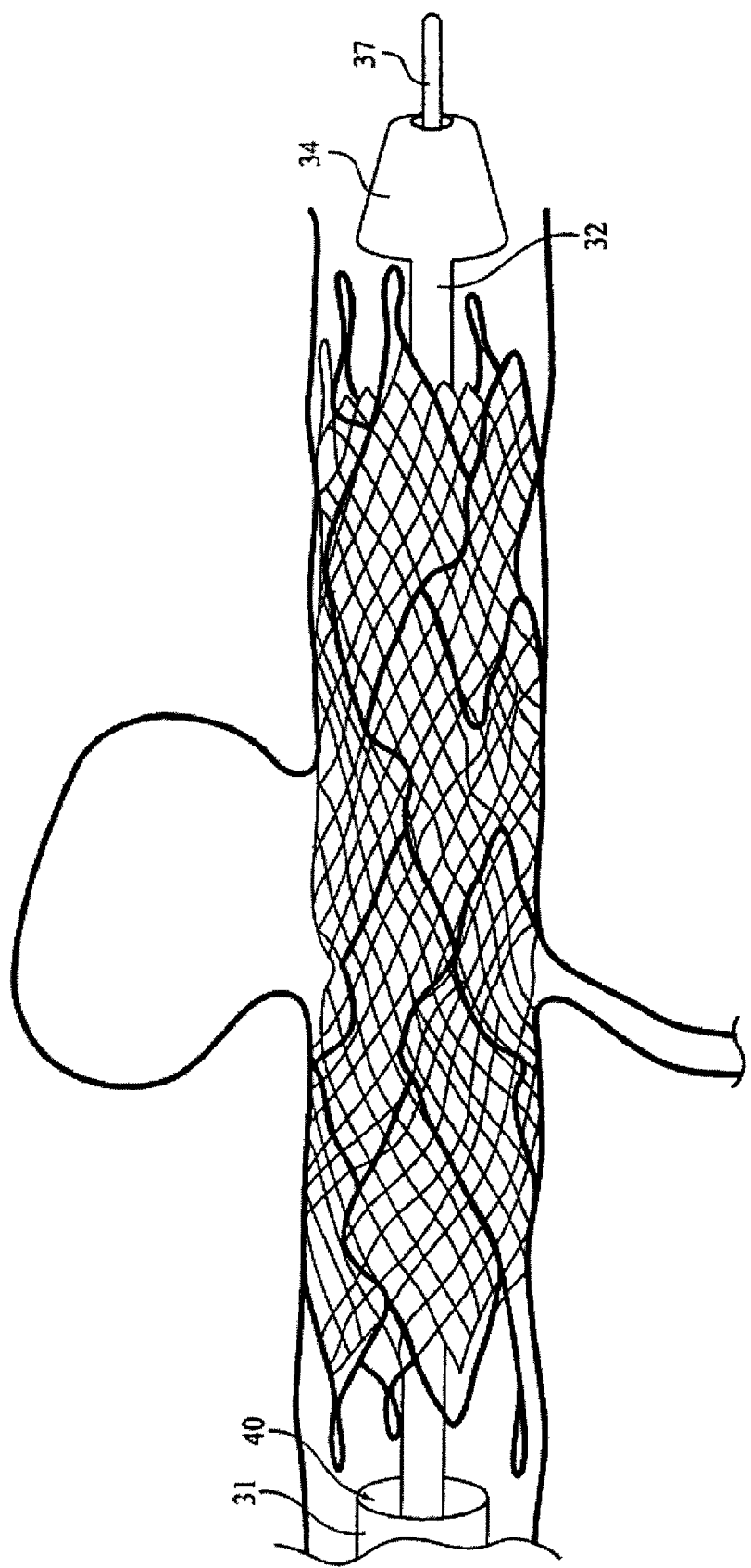
FIG. 2b is a side view of the distal portion of the deployment device subsequent to radial expansion of the endoprosthesis adjacent the aneurysm.

Referring to FIGS. 2a and 2b, endoprosthesis 100 is deployed to aneurysm 25 using a deployment device 30, such as a catheter that can be threaded through a tortuous pathway. The device 30 includes a retractable outer sheath 31 and an inner catheter 32. Device 30 is introduced over a guide wire 37 extending along the interior 28 of vessel 26. During introduction, the endoprosthesis 100 is radially compacted between outer sheath 31 and inner catheter 32 adjacent a distal opening 40 of the outer sheath.

Referring particularly to FIG. 2b, the outer sheath 31 is retracted upon reaching the desired deployment site, e.g., aneurysm 25. In some embodiments, endoprosthesis 100 self-expands by its own internal elastic restoring force when the radially restraining outer sheath is retracted. Alternatively, or in combination with self-expansion, deployment of prosthesis 100 may include use of a balloon or other device to radially expand prosthesis 100 within vessel 26. After deploying the endoprosthesis, the inner catheter 32 and guide wire 37 are withdrawn from vessel 26. Suitable delivery systems include the Neuroform, Neuroform2, and Wingspan Stent System available from Boston Scientific Target Therapeutics, Fremont, Calif. In embodiments, the outer sheath and/or inner catheter includes a reinforcing member to respectively resist elongation or compression as the outer sheath is withdrawn. Such reinforcing members include polymer shafts, braids, and coil structures.

Upon expansion, endoprosthesis 100 assumes a shape and radial extent generally coextensive with an inner surface of the vessel 26, e.g., a tubular shape centered about a longitudinal axis al of the prosthesis (FIG. 1). Depending upon the application, prosthesis 100 can have a diameter d of between, for example, 1 mm to 46 mm. In certain embodiments, a prosthesis for deployment within a vessel at an aneurysm can have an expanded diameter d of from about 2 mm to about 6 mm, e.g., about 2.5 mm to about 4.5 mm. Depending upon the application, prosthesis 100 can have a length along axis al of at least 5 mm, at least 10 mm, e.g., at least about 30 mm. An exemplary embodiment has an expanded diameter of about 3.5 mm and a length of about 15 mm. In embodiments, the stent body has a closed cell framework, an open cell framework, a helical framework, a braided framework, or combination thereof.

The cover can be fixed to the stent by, e.g. fasteners. Attachment techniques include brazing, welding or attachment with a filament, rivets or grommets, or crimping, or adhesive. In some embodiments, the tubular member differs from a fabric at least in that the tubular member lacks fibers that can be pushed apart to receive a filament as by sewing a fabric. Accordingly, the fenestrations can be formed prior to the process of passing the filament through the tubular member. Fenestrations that receive the filaments can be formed by, e.g., etching, laser cutting, or a photolithographic process. Attachment techniques are described in U.S. Ser. No. 11/025,866, titled MEDICAL DEVICES INCLUDING METALLIC FILMS AND METHODS FOR MAKING SAME, filed contemporaneously herewith, which application is incorporated herein by reference.

The cover is formed of a thin film that exhibits advantageous properties such as strength, toughness, and flexibility by selection of the composition of the film, processing techniques, and mechanical configuration. For example, in particular embodiments, the film is a vapor-deposited material composed of a nickel-titanium alloy having a strength additive, e.g. chromium. The film has a thickness of about 50 µm or less, e.g. about 4-35 µm, and includes fine fenestrations, which facilitate collapsing the film to small diameter for delivery into the body and expansion at the treatment site, while impeding blood access to the aneurysm. In particular embodiments, the film is processed to modify dislocations, which contribute to strength and toughness of the thin film.

Deposited materials are formed by depositing film constituents from a suspended state, e.g. in a vapor or a vacuum onto a surface. In embodiments, the constituents are suspended, e.g. by bombarding, heating or sputtering a bulk target. The suspended constituents deposit on a substrate to form the film. Deposited films can exhibit highly uniform thickness and microstructure in very thin films, e.g. about 50 µm or less, e.g. 4-35 µm. Deposition techniques include sputter deposition, pulsed laser deposition, ion beam deposition and plasma deposition. Suitable deposition processes are described in Busch et al. U.S. Pat. No. 5,061,914, Bose et al. U.S. Pat. No. 6,605,111, Johnston U.S. Pat. No. 6,533,905, and Gupta et al. U.S. 2004/0014253, the entire contents of all of which are hereby incorporated by reference.

In particular embodiments, the deposited film is an alloy that includes nickel and titanium, and a strength additive or additives, which modify a mechanical property, e.g., a hardness or elasticity, of the film. In particular embodiments, the film is a tertiary alloy that has substantially no other components besides nickel, titanium, and additive present in an amount greater than 1%, 0.5% or 0.2% or less than 20%, 10%, or 5% by weight of the film. The film may consist essentially of nickel, titanium, and chromium. In embodiments, the deposited film includes between 54 and 57 weight percent nickel with the balance composed essentially of titanium and chromium. In some embodiments, a ratio of a weight of chromium of the film to a combined weight of nickel, titanium, and chromium of the film is at least 0.001, at least 0.002 e.g., at least 0.0025. The ratio of the weight of chromium of the film to the combined weight of chromium, nickel, and titanium of the film can be 0.02 or less, 0.01 or less, e.g., 0.0075 or less. The ratio of the weight of chromium to the combined weight of chromium, nickel, and titanium of the film can be about 0.0025. In embodiments, the alloy exhibits superelastic or pseudo-elastic properties. Superelastic or pseudo-elastic metal alloy, as described, for example, in Schetsky, L. McDonald, "Shape Memory Alloys," Encyclopedia of Chemical Technology (3rd ed.), John Wiley & Sons, 1982, vol. 20. pp. 726-736; and commonly assigned U.S. Ser. No. 10/346,487, filed Jan. 17, 2003.

A metallic film can be combined with one or more filaments in an endoprosthesis cover. Because the filaments and film may have very different mechanical properties, e.g., elongation before break and tensile strengths, the filaments and film cooperate to lend the cover desirable mechanical properties, e.g., toughness along the circumferential, radial, and/or longitudinal dimensions. In embodiments, a filament secures portions of a film relative to other portions of the film such as to maintain the three-dimensional shape of the cover and/or to secure the film with respect to a stent body.

Figure 3A:
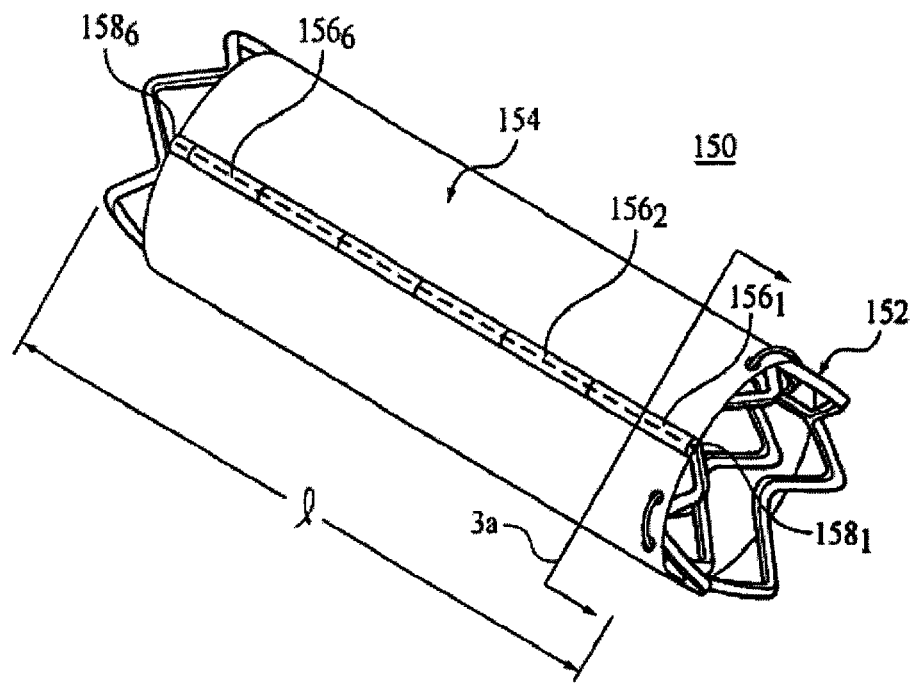
FIG. 3a is a perspective view of an endoprosthesis.
Figure 3B:
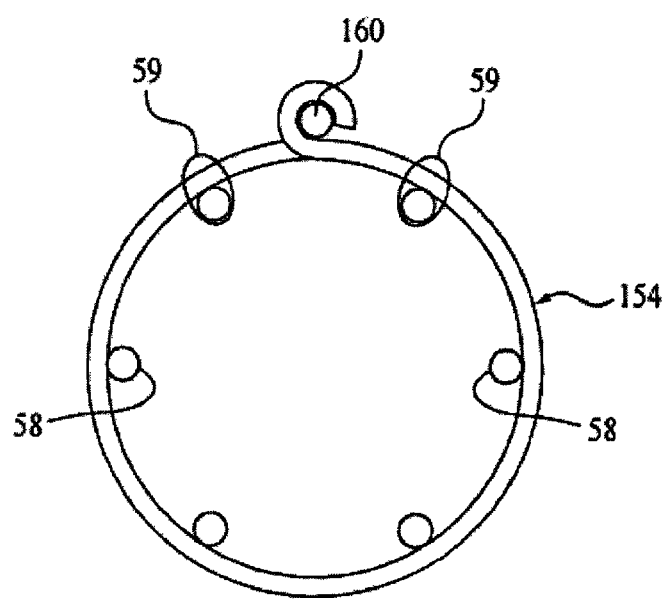
Figure 4:
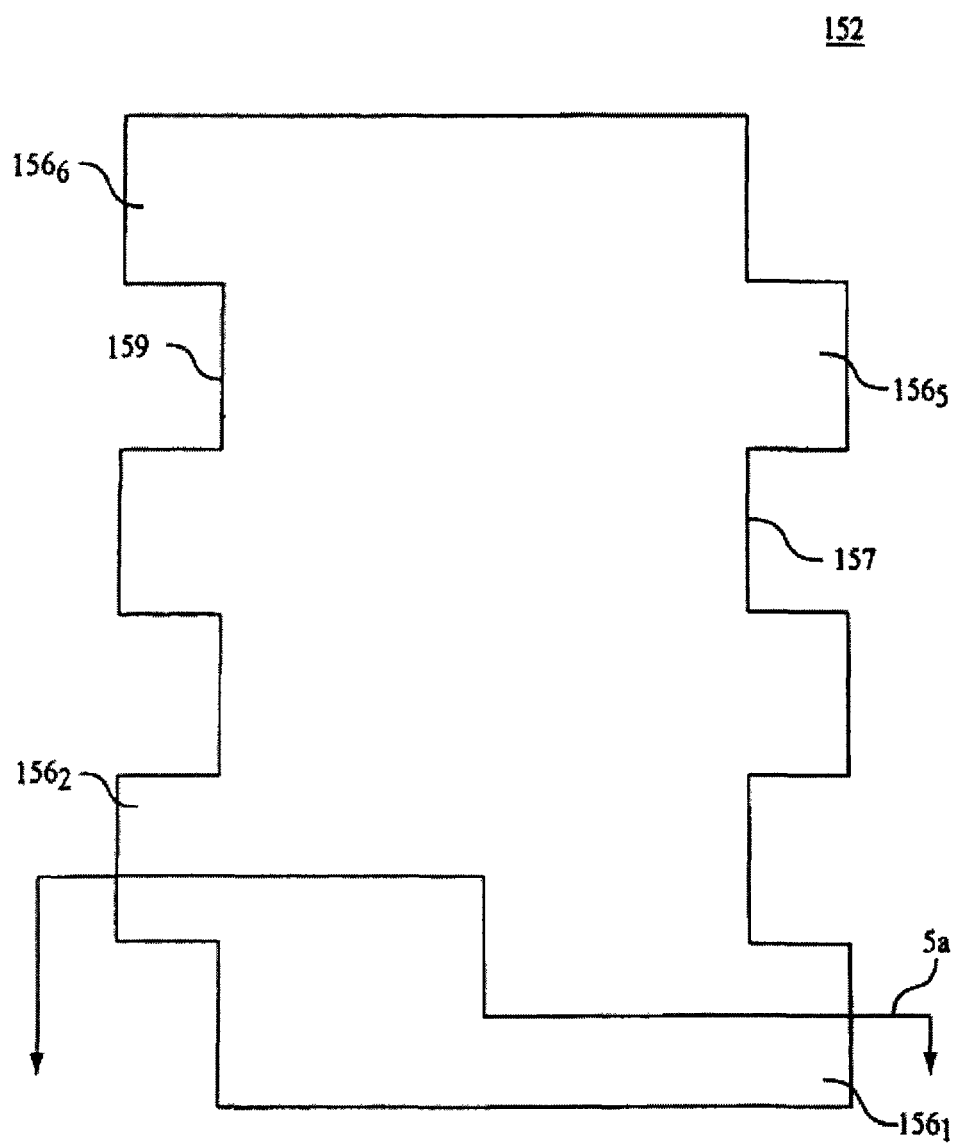
FIG. 4 is a top view of a cover of the endoprosthesis of FIG. 3a. The cover is shown in two-dimensions and separate from the endoprosthesis.

Referring to FIGS. 3a, 3b, and 4, an endoprosthesis 150 includes a cover 154 encircling a stent body 152. First and second edges 157 and 159 of cover 152 define a plurality of offset tabs 156i (FIG. 4). When formed as a cover, each tab defines a respective channel 158i (FIG. 3a). Different channels 158i are coaxial with one another parallel to a length l of cover 152. A filament 160 seen in FIG. 3b extends within the coaxial channels along the length l and prevents cover 154 from unrolling by securing offset tabs 156i relative to one another.

Filament 160 can include, e.g., a suture, a polymer, a textile, or a metal, e.g., a metal wire formed of gold, platinum, stainless steel, or a shape memory metal, e.g., nitinol. A filament can include a combination of such materials, e.g., a composite. The filament can be braided and need not have a circular configuration, e.g., the filament can be ribbon shaped. The filament typically has a thickness or radial dimension of less than a thickness of the film. In embodiments, the member is a metal wire having a diameter of about 10 µm or less, about 8µ, e.g., about 5 µm or less.

The filament 160 can have a higher tensile strength than the film of the cover 154. In embodiments, a ratio of the tensile strength of the filament 160 to the tensile strength of the film is at least about 1.5, e.g., at least about 2. The ratio may be about 4 or less, e.g., about 3 or less. The filament may be a nitinol wire having a tensile strength of at least 200 ksi, at least 250 ksi, e.g., at least 300 ksi. An exemplary metallic film has a tensile strength of 150 ksi.

In some embodiments, the filament 160 includes a wire of shape memory metal that is shape set differently from a shape set of the metallic film. In some embodiments, one of the member 160 and metallic film is shape set at a configuration corresponding to the radially compressed state within a delivery device while the other of the member and film is shape set at a configuration corresponding to the radially expanded state within a body passage. A primary difference in the shape set between the member 160 and the cover may be in the shape set length, with one of the member and cover having a longer shape set length than the other.

Figure 5A:
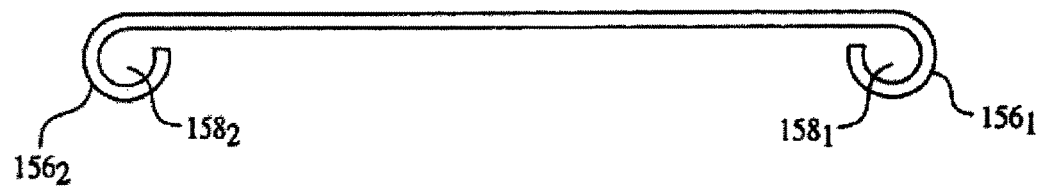
FIG. 5a is a cross-sectional end view of the cover of FIG. 4. Tabs of the cover have been formed into channels.
Figure 5B:
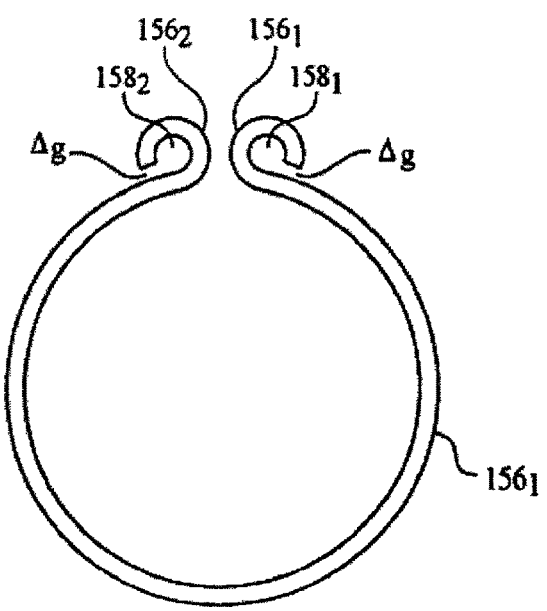
FIG. 5b is the cover of FIG. 5a. The cover has been formed into a generally tubular shape.

An exemplary method of manufacturing cover 154 includes depositing a metallic film on a substrate. The cover can be provided with fenestrations 62, which are not shown in FIG. 3a. Tabs 156i can be formed by photolithography or machined, e.g., by laser cutting, from a larger deposited film. Referring to FIG. 5a, each tab 156i is turned about itself to form a respective channel 158i. Referring to FIG. 5b, if not deposited on a three-dimensional substrate, the film can be rolled, e.g., about a mandrel, to provide a three-dimensional shape.

Adjacent tabs 156i are relatively secured by filament 160. The filament 160 can be inserted along the common axis of channels 158i or inserted laterally through a terminal gap Δg of each tab. If present, the terminal gap of each tab can be closed after introducing member 160. Either before or after positioning filament 160 with respect to tabs 156*i*, film 154 can be disposed with respect to a stent body, e.g., about the stent body (FIG. 3*b*). The cover and stent body can be relatively secured with, e.g., one or more filaments 59, which pass through fenestrations of the cover and engage framework members 58 of the stent body. In embodiments, some or all of the tabs engage a portion of the stent body, e.g., a framework member 58, to secure the cover and stent body.

In some embodiments, filament 160 and some or all of tabs 156*i* have little or no relative freedom of movement. For example, each tab 156*i* may mechanically engage filament 160 via a tight fit between respective channel 158*i* and the member 160. An adhesive or other polymer may also or alternatively be used to enhance the engagement between the filament and the channels of the tabs.

In embodiments, filament 160 and some or all of channels 158*i* allow some relative freedom of movement, e.g., longitudinal or circumferential freedom of movement. During radial compression and expansion of an endoprosthesis, the cover 154 and filament 160 move relatively to accommodate different length changes without deforming the cover or endoprosthesis. Longitudinal freedom of movement may be provided by a filament not tightly engaged by the channels, e.g., by a filament having a diameter smaller than an inner diameter of the channels. Circumferential freedom of movement can be provided by circumferentially elongating the channels so that the cover edges 157,159 can move circumferentially relative to one another, e.g., toward and away from one another. Adjacent tabs 156*i* and 156*i*±1 may define gaps (not shown) to allow the cover edges some relative longitudinal freedom of movement. An elastic polymer may fill the channels to help retain the filament yet allow some relative movement.

Channels 158*i* are shown as extending coaxially the entire length of the cover. In some embodiments, channels 158*i* extend along only a portion of the cover length, e.g., ½ the length or less, ⅓ the length or less, or ¼ the length or less. The resulting "shorter" channel may be located anywhere along the length of the endoprosthesis, e.g., centrally or distally or proximally relative to an implanted prosthesis.

Channels 158*i* are shown as generally parallel with a longitudinal axis of the endoprosthesis 150. In embodiments, the channels 158*i* and filaments can have other configurations, e.g., circumferential, curved, or helical about the endoprosthesis.

Figure 6:
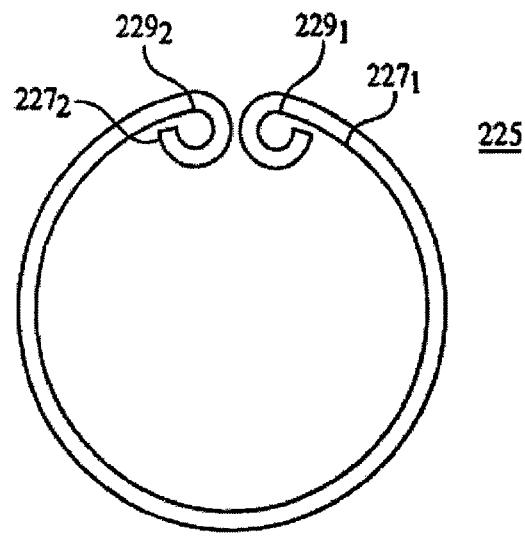
FIG. 6 is a cover suitable for an endoprosthesis. The cover includes tabs forming channels, which are located within a circumference of the cover.

Referring to FIG. 6, a cover 225 includes tabs 227*i* and channels 229*i* located within an external circumference of the cover. Accordingly, when relatively secured and placed concentrically with respect to a stent body, the cover forms a relatively smooth outer surface with little or no ridge-like protrusion resulting from the tabs 227*i*. Channels 229*i* may also be used to engage a framework member 58 of a stent body, which engagement can secure the cover and stent body.

Figure 7:
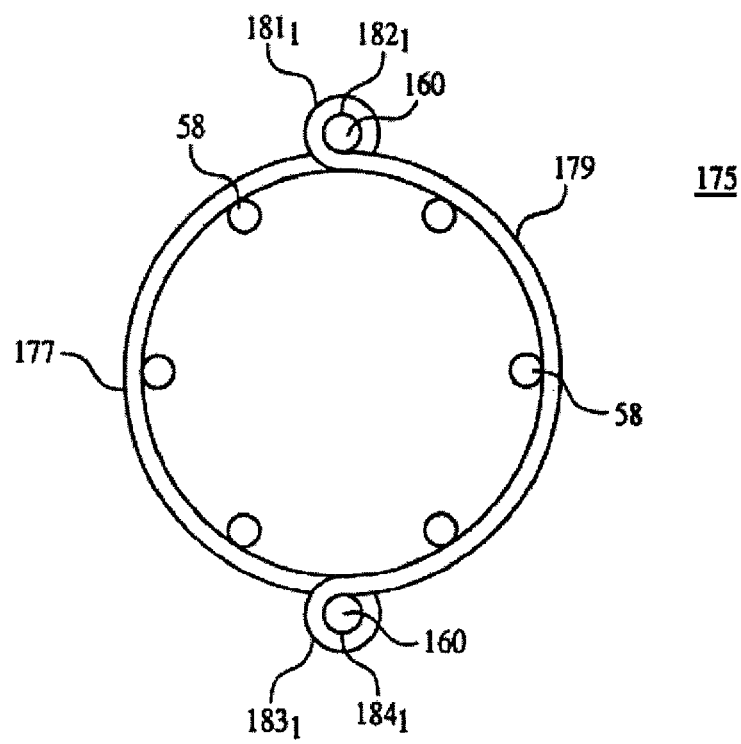
FIG. 7 is an endoprosthesis having a cover formed of two cover portions.

Referring to FIG. 7, a cover 175 having first and second cover portions 177,179 encircles a stent body having framework members 58. Each cover portion defines first and second edges. First edges and second edges of cover portions 177,179 are secured to one another by first and second sets of offset tabs 181*i*,183*i*, which form respective channels 182*i*,184*i*. The channels of different tabs are coaxial aligned and extend along at least a portion of the length of the endoprosthesis. A filament 160 extends along the coaxial channels. Although only two cover portions are shown, an endoprosthesis can have even more cover portions, e.g., 3 or more, 4 or more, or 5 or more, which combine to form a generally tubular cover.

Cover portions 177,179 may have some freedom of movement relative to one another. For example, by allowing longitudinal or circumferential freedom of movement between different cover portions, an endoprosthesis can accommodate delivery or deployment within a tortuous body passage having small radius curves. Freedom of movement between the cover portions can be provided using, e.g., the techniques described for providing relative freedom of movement between a filament and cover.

Figure 8:
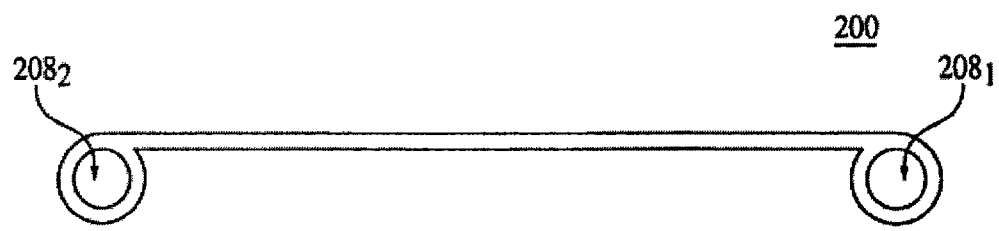
FIG. 8 is a cover having channels formed via metallic film deposition.
Figure 9:
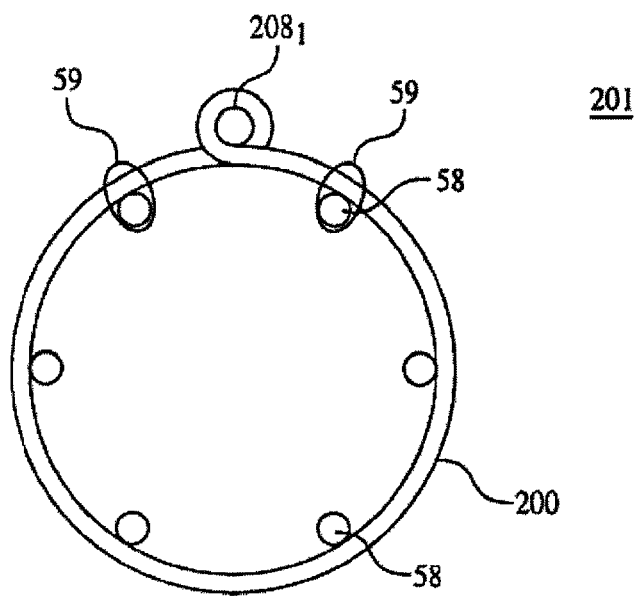
FIG. 9 is a cross-sectional view of an endoprosthesis including the cover of FIG. 8.

Referring to FIGS. 8 and 9, an endoprosthesis cover 200 includes tabs having integral channels 208*i* formed by, e.g., three-dimensional deposition over a sacrificial medium. Each integral channel defines a complete circumference without a seam resulting from mechanical channel formation. An endoprosthesis 201 is formed by positioning the cover 200 about a stent body having framework members 58 and securing the tabs with a filament 160 (FIG. 9).

An exemplary method of manufacturing cover 200 includes depositing a first layer of metallic film on a substrate, whether two- or three-dimensional. A sacrificial medium, e.g., chromium, is photolithographically deposited over portions of the previously deposited film. The sacrificial medium is formed of a material, e.g., chromium, that can be removed, e.g., by etching, from the metallic film without damage thereto. Additional material of the metallic film is deposited over the sacrificial medium to complete the film. Subsequently, the sacrificial medium is removed from the remaining film leaving behind the integral channels.

Figure 10A:
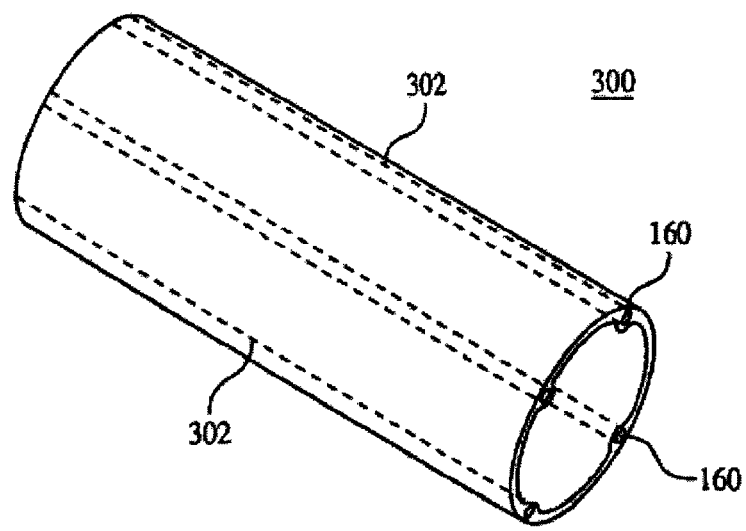
FIG. 10a shows an endoprosthesis having a plurality of integral, longitudinally extending filaments.
Figure 10B:
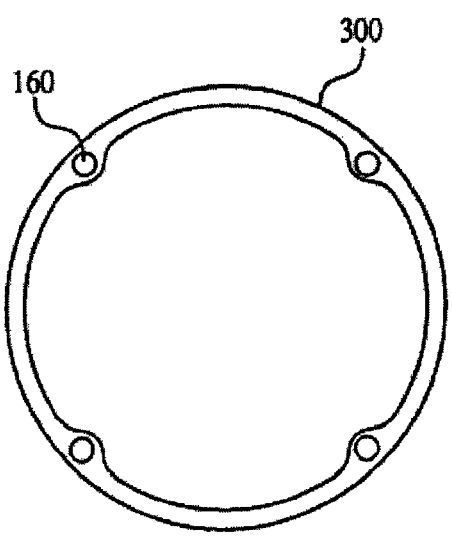

Referring to FIGS. 10*a* and 10*b*, a cover 300 (shown without a stent body) includes longitudinal channels 302 each formed by depositing metal about a filament 160. In this embodiment, the filament is typically a metal ribbon or wire, e.g., a metal wire of shape memory alloy. Depositing the metallic film about the wire secures the two together and ensures that the mechanical properties of each are communicated to the other without losses resulting from slippage. Although filaments 160 are shown as extending linearly along the longitudinal axis of the endoprosthesis, one or more of the filaments can have other longitudinally extending configurations, e.g., circumferential, curved, or helical. Filaments may intersect or cross one another. In other embodiments, some or all the wires do not intersect or cross another wire.

An exemplary method for forming cover 300 includes depositing a first layer of metallic film. Wires 160 are positioned adjacent the deposited film. Additional metal is deposited over the wires to integrate the wires and film. In an alternative method, wires 160 are positioned over a substrate. A first amount of metallic film is deposited over the wires and substrate. Subsequently, the first amount of film and substrate are separated and additional metal film is deposited to integrate the wires and film.

Figure 11:
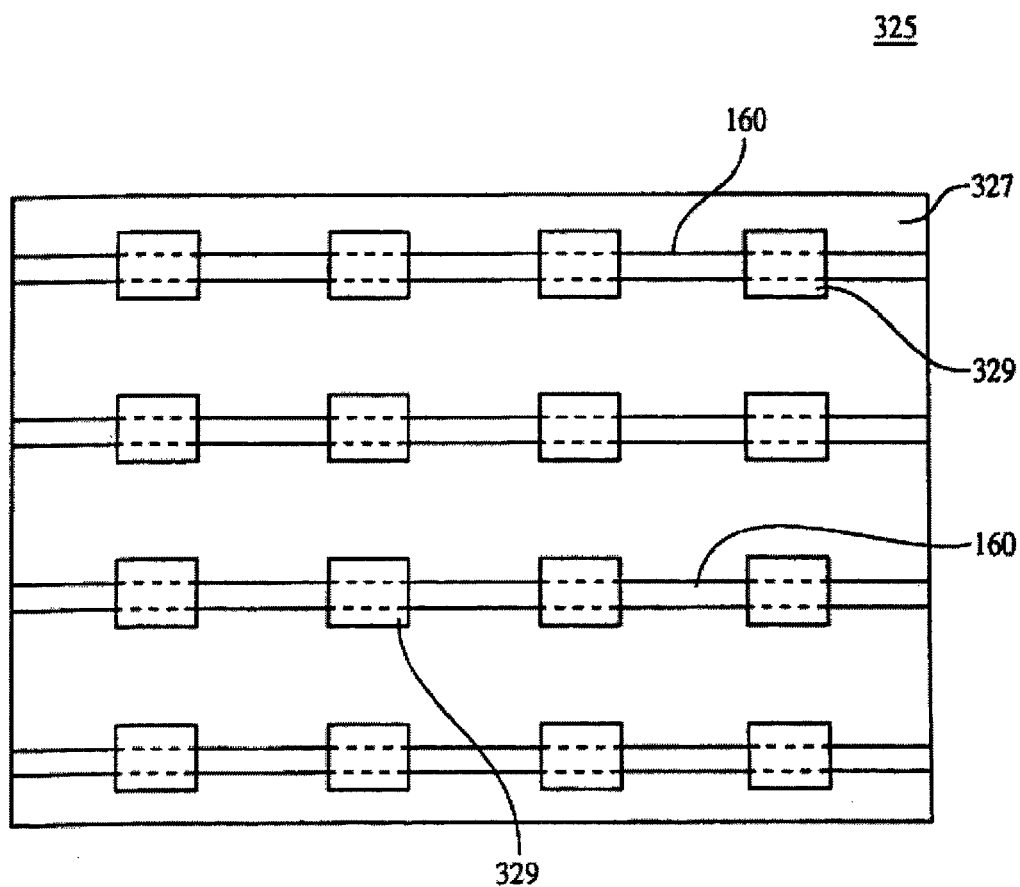
FIG. 11 is a cover suitable for an endoprosthesis. The cover has a plurality of longitudinally extending filaments each having a plurality of embedded integral portions and a plurality of exposed portions.

Referring to FIG. 11, a cover 325 includes a plurality of partially exposed filaments 160. Portions of the filaments 160 are embedded within a deposited metallic film of the cover and other portions of the filaments are left exposed. When formed about a stent body, the exposed portions of wire 160 can engage framework members of the stent body to secure the cover and stent body together. Another filament, e.g., a suture or wire, can be threaded through exposed portions of filaments 160 to secure the cover to a stent body or to retain the cover in a three-dimensional shape.

In some embodiments, a deposited thin film and including one or more filaments is useable as an endoprosthesis without a supporting stent. For example, an endoprosthesis without a supporting stent can include a deposited thin film including one or more at least partially embedded wires contributing to radial and/or longitudinal strength of the film.

In some embodiments, the filaments, whether embedded or not, extend beyond an end of the endoprosthesis. The extending filaments can be used to, e.g., re-sheath the endoprosthesis in order to change its position or withdraw it from a lumen, or to pull the endoprosthesis along a body lumen.

In the embodiment shown, an endoprosthesis has a generally tubular shape. In some embodiments, however, the endoprosthesis (or stent body 52 or tubular member 54 individually) has or includes other shapes such as conical, oblate, and branched. The endoprosthesis may have a closed end to form, e.g., a basket shape. Thin films, discussed above, composed of Ni—Ti-strength additive alloys and/or with modified microstructures, can be used in other applications. Examples include baskets, filters, catheters, guidewires, and medical balloons, such as an angioplasty balloon. Filaments of such endoprostheses may intersect or be woven to define a shape of the endoprostheses.

Other examples of endoprostheses including a thin film as well as related systems and methods are described in U.S. provisional patent application No. 60/549,287, filed Mar. 2, 2004, which application is incorporated herein by reference.

An endoprosthesis may include a cover disposed externally to a framework as shown and/or internally of a framework. Endoprostheses having a cover including, e.g., a deposited thin film, disposed internally of a framework are described in U.S. patent application Ser. No. 11/025,464, titled MEDICAL DEVICES INCLUDING METALLIC FILMS AND METHODS FOR MAKING SAME, and filed concurrently herewith, which application is incorporated herein by reference.

An endoprosthesis may include features to enhance a flexibility of the endoprosthesis as described in U.S. patent application Ser. No. 11/025,158, titled MEDICAL DEVICES INCLUDING METALLIC FILMS AND METHODS FOR MAKING SAME, and filed concurrently herewith, which application is incorporated herein by reference.

The composition and/or fabrication method of a deposited thin film of an endoprosthesis may include features that enhance a strength or toughness of the film as described in U.S. patent application Ser. No. 11/025,860, titled MEDICAL DEVICES INCLUDING METALLIC FILMS AND METHODS FOR MAKING SAME, and filed concurrently herewith, which application is incorporated herein by reference.

An endoprosthesis may include a deposited thin film and a polymer as described in U.S. patent application Ser. No. 11/025,867, titled MEDICAL DEVICES INCLUDING METALLIC FILMS AND METHODS FOR MAKING SAME, and filed concurrently herewith, which application is incorporated herein by reference.

Methods for loading an endoprosthesis into a delivery device and systems for delivering an endoprosthesis to a treatment site are described in U.S. patent application Ser. No. 11/025,660, titled MEDICAL DEVICES INCLUDING METALLIC FILMS AND METHODS FOR LOADING AND DEPLOYING SAME, which application is incorporated herein by reference.

All publications, references, applications, and patents referred to herein are incorporated by reference in their entirety.

Other embodiments are within the claims.

What is claimed:

1. An endoprosthesis, comprising:
a framework;
a cover on the framework, the cover comprising at least one deposited metallic film and at least one fenestration, the cover defining first and second opposed metallic film edges, the first and second opposed metallic film edges each defining a channel that together extend along at least a portion of the metallic film edges;
at least one first filament, the at least one first filament extending through the channel of each opposing metallic film edge; and
at least one second filament, wherein the second filament passes through the at least one fenestration.

2. The endoprosthesis of claim 1, wherein the deposited metallic film comprises nickel and titanium.

3. The endoprosthesis of claim 1, wherein the framework and the cover have a substantially tubular shape defining a longitudinal axis and the at least one first filament extends generally parallel to the longitudinal axis.

4. The endoprosthesis of claim 3, wherein the tubular shape defines a length along the longitudinal axis and the length of the first filament is at least about 30% of the length of the shape.

5. The endoprosthesis of claim 3, wherein the framework is a stent body, at least a portion of the at least one first filament and at least a portion of the stent body being secured together.

6. The endoprosthesis of claim 3, wherein the first filament defines a longitudinal axis, an engagement between at least one of the channels and the first filament restricting movement of the first filament along its longitudinal axis with respect to the at least one of the channels.

7. The endoprosthesis of claim 1, wherein the first and second opposed edges each define at least one offset tab, the channel of each opposed edge being formed by the offset tab.

8. The endoprosthesis of claim 1, wherein the first and second opposed edges each define a plurality of channels, each channel being formed by a respective offset tab, the first filament extending through at least some of the channels of each opposed edge.

9. The endoprosthesis of claim 1, wherein the first and second opposed edges are a first pair of opposed edges and the metallic film of the cover defines a plurality of pairs of first and second opposed edges, each edge of each pair defining at least one channel, a respective first filament extending through the channel of each opposed edge of each pair.

10. The endoprosthesis of claim 9, wherein each pair of opposed edges extends generally along the longitudinal axis and each first filament has a length at least about 30% of the length of the tubular shape.

11. The endoprosthesis of claim 10, wherein the first and second edges of each pair of opposed edges have at least some relative freedom of movement with respect to a circumference of the cover.

12. The endoprosthesis of claim 1, wherein the deposited metallic film is a tertiary alloy comprising nickel, titanium, and an additive in an amount between 0.2% and 20% by weight of the film.

13. The endoprosthesis of claim 12, wherein the additive is chromium.

14. The endoprosthesis of claim 1, wherein the at least one first filament is formed of gold, platinum, stainless steel, or a shape memory metal.

15. The endoprosthesis of claim 1, wherein the at least one first filament is a suture, polymer, textile, metal, or a composite thereof.

16. The endoprosthesis of claim 1, wherein the at least one first filament has a circular cross section, is braided, or has a ribbon shape.

17. The endoprosthesis of claim 1, wherein the at least one first filament is a metal wire having a diameter of about 10 µm or less.

18. The endoprosthesis of claim 1, wherein the at least one first filament has a configuration that is circumferential, curved, or helical about the endoprosthesis.

19. The endoprosthesis of claim 1, wherein the deposited metallic film has a thickness of about 4-35 µm.

20. The endoprosthesis of claim 1, wherein the first and second opposed metallic film edges each defining a channel that together extend along at least half of the length of the metallic film edges.

* * * * *